United States Patent [19]
Trull et al.

[11] Patent Number: 6,080,136
[45] Date of Patent: Jun. 27, 2000

[54] ANGIOGRAPHIC SYRINGE ADAPTER FOR FRONT-LOADING INJECTOR

[75] Inventors: Michael Wayne Trull, Apex; Richard L. Abbott, Durham, both of N.C.

[73] Assignee: PolyTen Plastics, LLC, Washington, N.C.

[21] Appl. No.: 09/096,442

[22] Filed: Jun. 11, 1998

[51] Int. Cl.[7] .................................................. A61M 5/315
[52] U.S. Cl. ...................... 604/218; 604/152; 128/DIG. 1
[58] Field of Search ..................... 604/218, 151, 604/152, 154, 155, 131, 187; 120/DIG. 1, 655

[56] References Cited

U.S. PATENT DOCUMENTS

| | | |
|---|---|---|
| 3,156,236 | 11/1964 | Williamson . |
| 3,631,847 | 1/1972 | Hobbs, II . |
| 3,880,138 | 4/1975 | Wootten et al. . |
| 4,006,736 | 2/1977 | Kranys et al. . |
| 4,582,218 | 4/1986 | Ross . |
| 4,677,980 | 7/1987 | Reilly et al. . |
| 4,846,796 | 7/1989 | Carrell et al. . |
| 4,846,797 | 7/1989 | Howson et al. . |
| 4,869,720 | 9/1989 | Chernack . |
| 4,911,695 | 3/1990 | Lindner . |
| 5,006,112 | 4/1991 | Metzner . |
| 5,007,904 | 4/1991 | Densmore et al. . |
| 5,155,960 | 10/1992 | Shannan . |
| 5,176,646 | 1/1993 | Kuroda . |
| 5,279,583 | 1/1994 | Shober, Jr. et al. . |
| 5,300,031 | 4/1994 | Neer et al. . |
| 5,383,858 | 1/1995 | Reilly et al. . |
| 5,520,653 | 5/1996 | Reilly et al. . |
| 5,535,746 | 7/1996 | Hoover et al. . |

*Primary Examiner*—John G. Weiss
*Assistant Examiner*—David J. Cho
*Attorney, Agent, or Firm*—Steven J. Hultquist; William A. Barrett

[57] ABSTRACT

A front-load syringe injector system includes a front-load injector apparatus having mounted on a front face thereof a detachably engageable adapter. A driving head is engaged with a drive mechanism of the injector and the driving head disengageably engages a plunger mounted in an angiographic syringe mounted on the adapter. At least one of the plunger and driving head and syringe elements interacts with the adapter to effect engagement and disengagement of the plunger and driving head and syringe with respect to one another.

48 Claims, 8 Drawing Sheets

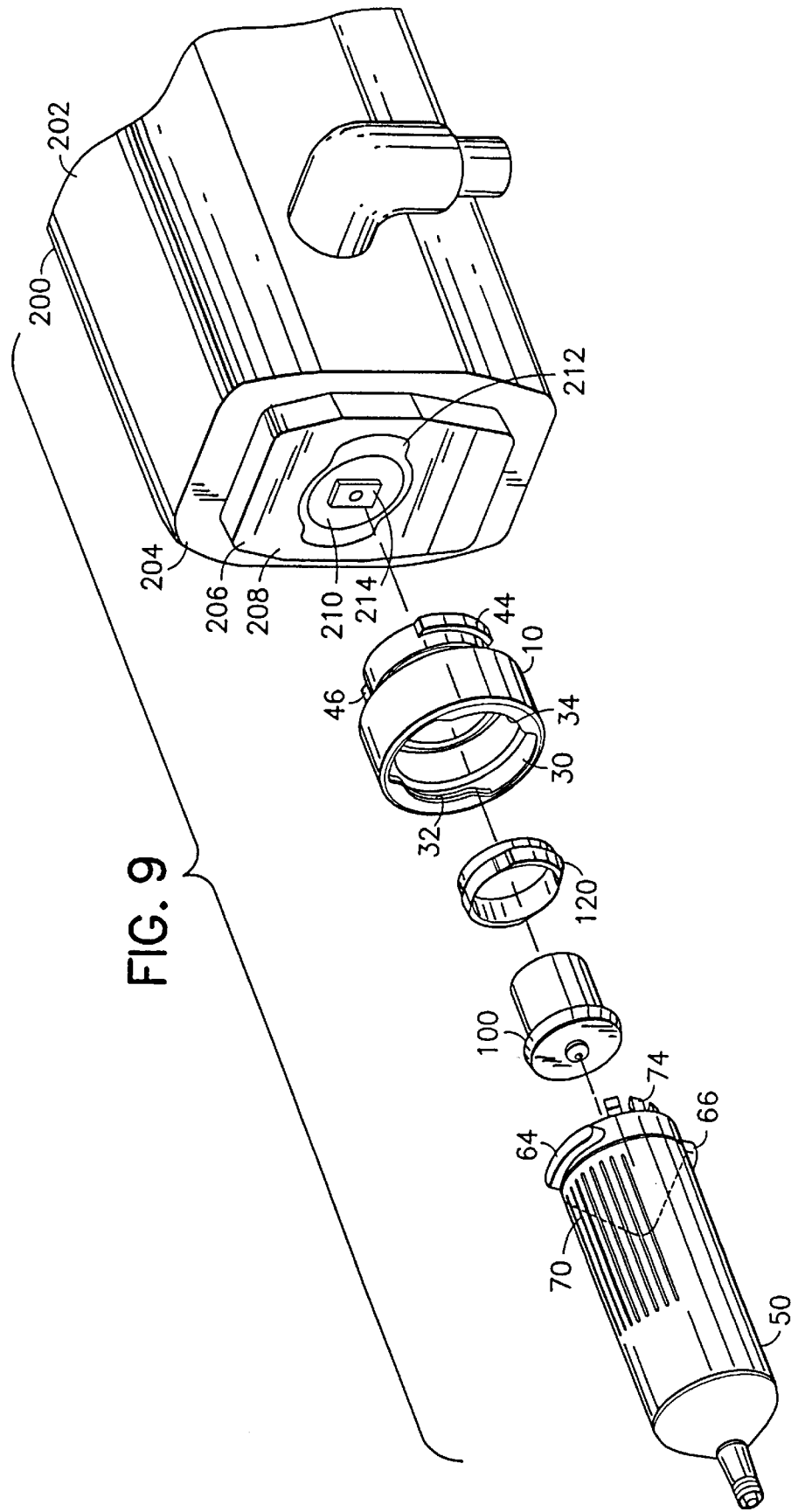

ANGIOGRAPHIC SYRINGE ADAPTER FOR FRONT-LOADING INJECTOR

BACKGROUND OF THE INVENTION

1. Field of the Invention

This invention generally relates to power-driven angiographic syringes, and specifically to an adapter and plunger for use with such a syringe, and to an adapter, plunger, syringe, and power injector system comprising same.

2. Description of the Related Art

In the field of angiography, a contrast medium of suitable indicating character (radiopacity) is introduced under pressure into coronary arteries, and the arterial network then is monitored by fluoroscopic or other visualizing means. As a result, arterial plaque deposits and/or other arterial occlusions are readily visually determined as to their size and location, so that suitable treatment methods, such as removal of the occluding material by lasing or mechanical excision, or by displacement techniques such as balloon angioplasty, may be carried out.

To effect the introduction of the contrast medium into the arterial network for angiographic study, it has been common practice to utilize injector syringes in combination with arterial catheters. The syringe may be machine-mounted in a so-called "power injector" apparatus, with the distal end of the syringe being connected to the catheter which is introduced into the arterial system to be studied.

There is disclosed in U.S. Pat. No. 4,677,980 issued Jul. 7, 1987 to D. M. Reilly, et al., an angiographic power injector featuring a rotating turret for housing multiple angiography syringes in readiness for injection. In use, the turret is selectively rotated to align an angiographic syringe with a driving mechanism of the power injector. Specifically, as is shown in FIGS. 9 and 10 of this patent, the plunger of the angiographic syringe may be configured with rearwardly extending hook members which are engaged by the head and stem portion (typically termed a "ram" in the field) of the driving mechanism.

In the plunger configuration disclosed in this patent, the hook elements on the proximal face of the plunger are diametrally opposed to one another, to form a slot therebetween through which the ram head is inserted and subsequently rotated. The head is of transversely extending character, so that it thereby engages the respective hook members. In this manner, the head and stem of the driving mechanism and the hook members are described to constitute a quick release driving connection, with the driving mechanism head fitting into the aperture formed by the hook members, and with the stem extending out from the aperture through the access slot between the hook members.

The Reilly et al. patent, at column 6, lines 24–52 thereof, describes the subsequent operation of the coupled syringe. First, the driving mechanism is forwardly translated to drive the plunger through the syringe to expel air therefrom. Next, the syringe is connected to a source of contrast media and the driving mechanism is retracted to pull the plunger back through the syringe, to draw contrast media thereinto. Finally, the driving mechanism is advanced to drive the plunger distally in the syringe and effect injection of the contrast media through a catheter attached to the syringe. The patent states that after the injection has been carried out, the driving mechanism may be disengaged from the plunger, without reversing its movement, by the simple expedient of rotating the driving mechanism 90°, so that the driving mechanism head extends from the aperture on either side (see FIG. 10 of the patent). Subsequent retraction of the driving mechanism results in the head and stem of the driving mechanism being withdrawn from the aperture and slot, thereby disengaging the driving mechanism from the plunger.

As a result of the foregoing configuration of the driving mechanism, and the hook members on the plunger, the risks incident to retracting the plunger through the syringe during the angioplasty procedure are said to be eliminated, and the mating hook members and driving mechanism head are said to cooperate so that the plunger can be placed in either a driven retractable state, or an undriven non-retractable state, at any time during the injection operation and at any position of the plunger, without substantial force being applied therebetween.

While the foregoing configuration of the hook members on the plunger facilitates the engagement and disengagement of the driving mechanism, without change in the position of the plunder, it also is true that the hook members themselves provide only a very small contact area for mating with the head of the driving mechanism, when the driving mechanism is in driving or retraction engagement with the hook members.

There is thus the danger that the head of the driving mechanism may disengage from contact with the hook members during operation of the syringe, so that subsequent rotation of the driving mechanism to effect disengagement actually effects re-engagement of the driving mechanism with the hook members, in turn causing retraction of the plunger, an occurrence which is specifically desired to be avoided.

The Reilly et al. patent discloses other plunger and driving mechanism constructions, e.g., as shown in FIGS. 11–21 of the patent, but all such alternative constructions are relatively more complex in construction and operation.

U.S. Pat. No. 5,007,904 issued Apr. 16, 1991 in the names of L. L. Densmore and T. A. Lindner, discloses an angiographic syringe plunger having a generally converging distal portion, and a rear face of which is provided a coupling structure which is transversely engageable by, and transversely disengageable from, a driving mechanism of a power-driven angiographic syringe. Once engaged by the driving mechanism, the plunger cannot be disengaged solely by rotation of the driving mechanism relative to the plunger in the absence of transverse translational movement of the driving mechanism and plunger relative to one another. The coupling structure disclosed in this patent includes a wall extending rearwardly from the proximal face of the plunger body and partially circumferentially thereon. The wall terminates at a proximal extremity, and a radially inwardly extending flange is joined at an outer peripheral portion thereof to the proximal extremity of the wall. In such manner, the radially inwardly extending flange and the wall form with the proximal face of the plunger a cavity transversely open to insertion of a ram head thereinto. For example, the coupling structure described in this patent may be generally C-shaped, with a continuously curved portion having an arc length not exceeding about 180°, and optionally provided with tangentially extending end segments respectively joined to the extremities of the continuously curved portion.

U.S. Pat. No. 4,199,695 issued Mar. 27, 1990 to Thomas A. Lindner discloses another plunger for a power-driven angiographic syringe assembly. The plunger includes a plunger body having a generally convergent distal portion and a proximal face. Laterally spaced-apart retention members are disposed on the proximal face in diametrally opposed relationship to one another, for retaining the power driving means in position once engaged with the plunger. Each of the retention members comprises a leg portion extending generally rearwardly from the proximal face and joined at a rearward part to a bridge segment laterally inwardly extending therefrom toward the other retention member, to an inner extremity, which is in spaced relationship to the corresponding inner extremity of the bridge segment of the other retention member. The inner extremities of the bridge segments thereby define a spacing accommodating transverse passage of the drive shaft therethrough. The leg portions and bridge segments of the retention members together define with the proximal face of the plunger a lateral slot accommodating transverse passage of the driving head therethrough. Transversely outwardly extending flexible, resilient flange elements are joined to the inner extremity of each of the aforementioned bridge segments and form laterally spaced-apart, transversely aligned pairs of flange elements on either side of the bridge segments, defining a transverse channel therebetween. The flange elements are shaped to define marginal portions of the transverse channel having a reduced channel width relative to a medial portion thereof. The marginal channel portions allow transverse passage of the drive shaft therethrough by deforming the flange elements bounding the marginal channel portions, so that the drive shaft thereafter is retentively held in the medial portion of the transverse channel, to accommodate free rotation of the driving mechanism relative to the plunger, without disengaging the driving mechanism from the plunger.

U.S. Pat. Nos. 5,383,858 and 5,520,653, issued Jan. 24, 1995 and May 28, 1996, respectively, to David M. Reilly, et al. describe a front-loading injector and syringe assembly, in which the syringe is mountable on and removable from a front wall of the injector housing. The front wall of the housing has a face plate presenting a pair of slots for receiving retaining flanges on the proximal end of the syringe. The syringe thus is inserted with the proximal end flanges passing through the slots, and then the syringe is rotated to engage the flanges behind associated retaining flanges of the face plate. The syringe contains a plunger with a proximal face having hook-like elements which engage with the ram tip of the injector apparatus. The ram tip is of elongate character and passes into the slot between the hook-like members on the proximal face of the plunger, so that subsequent rotation of the syringe into locking position engages the hook-like members with the end portions of the ram tip.

An object of the present invention is to provide an adapter for syringes of different manufacturers to be used on a front-loading injector apparatus.

It is an another object of the present invention to provide an improved frontloading syringe and injector apparatus comprising same, for injection of liquid contrast media or other fluid.

It is another object of the present invention to provide a plunger which is readily engageable with the driving mechanism of a front-load power injector system, without the necessity for registration and rotational locking.

It is yet another object of the present invention to provide a plunger structure which avoids any contamination of the internal surfaces of the syringe during loading of the syringe with contrast fluid or other media to be dispensed therefrom.

Other objects and advantages of the present invention will become more fully apparent from the ensuing disclosure and appended claims.

SUMMARY OF THE INVENTION

In a broad aspect, the present invention relates to a front-load syringe injector system including a front-load injector apparatus having mounted on a front face thereof a detachably engagable adapter, with a driving head engaged with a drive mechanism of the injector and such driving head disengageably engaging a plunger mounted in an angiographic syringe mounted on the adapter, wherein at least one of the plunger and driving head and syringe elements interacts with the adapter to effect engagement and disengagement of the plunger and driving head and syringe with respect to one another.

In one specific aspect, the present invention relates to an adapter for an angiographic syringe having utility in a power-driven angiographic front-loading syringe assembly comprising power driving means including an axially extending reciprocatable driving shaft and a frustoconical shaped driving head attached to the drive shaft.

The adapter includes a main body having a rear cylindrical extension, with a central bore extending through the main body and the rear cylindrical extension. The rear cylindrical extension includes diametrally opposed flanges for engaging a matably shaped cavity on a front face of an injector apparatus, and lockable in position by rotation of the main body so that the diametrally opposed flange elements engage retaining flange elements in the face of the injector apparatus. The main body includes a front slot opening communicating with the central bore, the front slot opening having diametrally opposed retention flange portions transverse to the slot opening, for engagement with a front-load syringe having rear flange members engageable with the slot opening and lockable in position in the main body by rotation so that the rear flange members of the syringe engage the retention flange portions of the main body. The main body also includes a lifting ring defining an annular volume between the central bore and the lifting ring for engagement with a rear circumferential extremity of a syringe. The rear cylindrical extension ma y include an outer surf ace circumferential groove, and has at least one locking means associated therewith, such as for example a leaf spring secured within the circumferential groove and cantilevering tangentially therefrom, so that during rotational engagement of the main body with the matably shaped cavity of the injector, features within the cavity depress the leaf spring, and when the main body is rotated to a final, installed position a recess in the injector cavity allows the leaf spring to flare outwardly and prevent backrotational removal of the adapter. Other locking, means may be employed, such as a pivot arm structure associated with a pocket or cavity in the cylindrical extension or other part of the adapter.

The main body may also include a means for sealing a rear face of the main body to the front face of the injector. In a specific embodiment, the means for sealing a rear face of the main body to the front face of the injector comprises an o-ring disposed in a circumferential groove in the rear face. Alternatively, the sealing means may comprise a gasket on a flat surface of the rear face, a flat washer on a flat surface of the rear face, or other sealing means of appropriate character.

In another specific aspect, the pre sent invention relates to a plunger for an angiographic syringe having utility in a power-driven angiographic front-loading syringe assembly comprising power driving means including an axially extending reciprocatable driving, shaft and a frustoconical shaped driving head attached to the drive shaft.

The plunger includes a plunger body having a generally convergent distal portion and a proximal face.

The plunger body has an outer circumferentially continuous edge surface for engaging an interior surface of a syringe barrel when the plunger is operatively positioned within the syringe barrel.

The proximal face of the plunger includes a circumferential surface portion. An array of diametrally opposed spaced-apart flexible resilient engagement members is joined to the circumferential surface portion of the proximal face of the plunger body and rearwardly extends therefrom. Each of the flexible resilient engagement members has a shank portion rearwardly extending from the circumferential surface portion and terminating in a tail hook portion including a transversely and radially inwardly extending retention surface for matably engaging with a rear circumferential surface of a drive head of an injector when the drive head is operatively coupled with the plunger. Each tail hook portion at the retention surface is of increased thickness relative to the shank portion of the flexible resilient engagement member and of tapering character toward a rearmost extremity thereof, with a convexly shaped inner engagement surface for contacting the frustoconical shaped drive head to circumferentially compressively engage a frustoconical side surface of the driving head with the transversely and radially inwardly extending retention surface matably engaged with a rear circumferential surface of the driving head when the driving head is engaged with the plunger. The array of diametrally opposed spaced-apart flexible resilient engagement members is arranged on the circumferential surface portion of the proximal face of the plunger so that the flexible resilient engagement members are radially inwardly spaced from the outer circumferentially continuous edge surface of the plunger, whereby the flexible resilient engagement members do not contact interior surfaces of the syringe barrel during translation of the plunger forwardly or rearwardly through the barrel.

A further aspect of the invention relates to an angiographic syringe including a plunger of the above-described type.

A further aspect of the invention relates to a retrofit kit including a plunger, syringe, and an adapter of the above-described type.

In a further aspect, the invention relates to a front-load injector system comprising an adapter and angiographic syringe including a plunger of the above-described construction.

Other aspects and features of the invention will be more fully apparent from the ensuing disclosure and appended claims.

BRIEF DESCRIPTION OF THE DRAWINGS

FIG. 9 is a perspective view of a retrofit kit of a general type as shown in FIG. 2, in exploded view relationship to a front face of a front-load syringe injector assembly, according to another aspect of the invention.

DETAILED DESCRIPTION OF THE INVENTION, AND PREFERRED EMBODIMENTS THEREOF

The disclosure of U.S. patent application Ser. No. 08/916,369 filed Aug. 22, 1997 for "FRONT-LOAD ANGIOGRAPHIC INJECTOR SYSTEM, ANGIOGRAPHIC SYRINGE AND PLUNGER FOR ANGIOGRAPHIC SYRINGE" is hereby incorporated herein by reference in its entirety.

Figure 1:
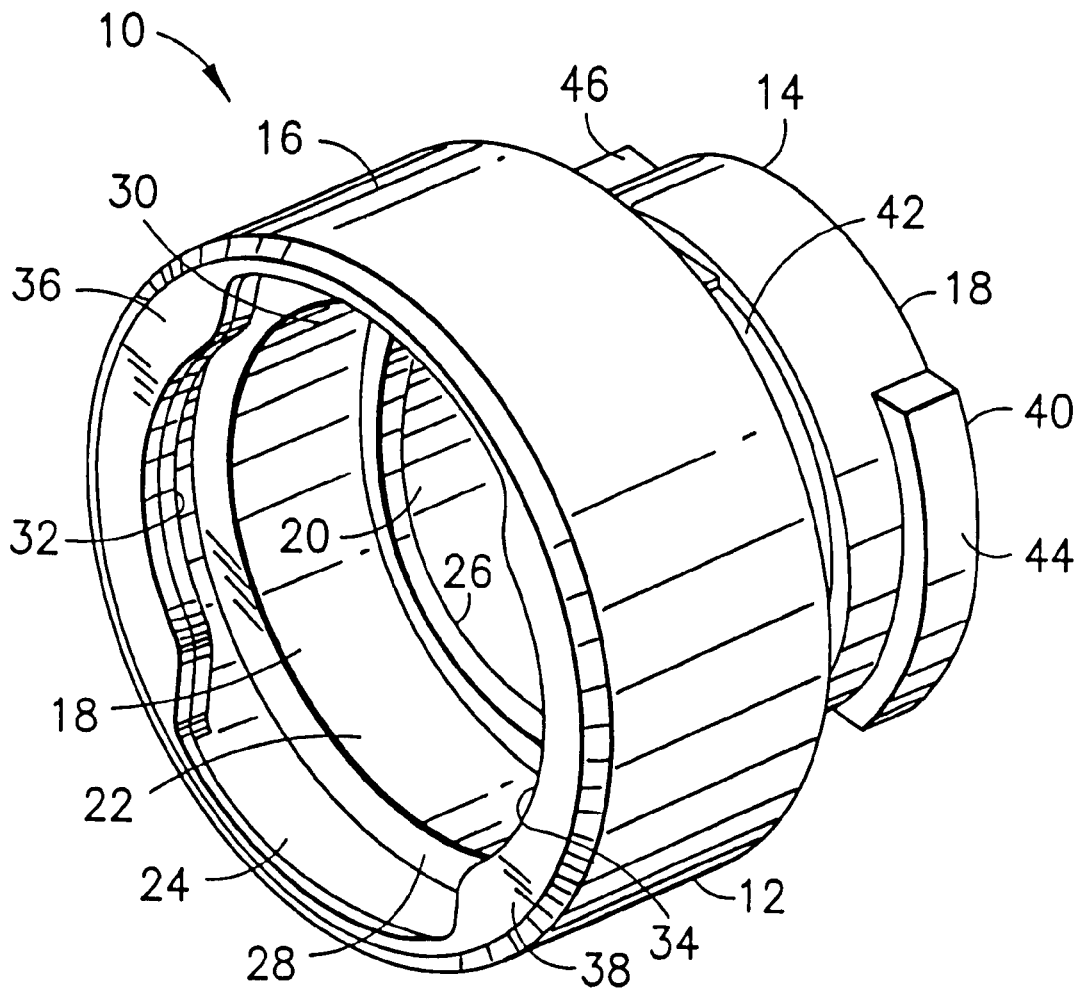
FIG. 1 is a perspective view of an adapter for interconnecting an angiographic syringe with an injector according to one embodiment of the present invention.

FIG. 1 is a perspective view of an adapter for interconnecting an angiographic syringe with an injector. The adapter 10 comprises a main body 12 and mounted thereon or integrally formed therewith is a rear cylindrical extension 14. Main body includes a generally cylindrical side wall surface 16. The adapter has a central bore 18 therein bound in the rear cylindrical extension by first bounding wall 20. Central bore 18 is bound in the main body by second bounding wall 22 and by third bounding wall 24. The first bounding wall 20 is of smaller diameter than second bounding wall 22, and the junction of such bore portions define a first annular rim 26 of the bore. The second bounding wall 22 is of smaller diameter than third bounding wall 24, and the junction of the second and third bore portions define a second annular rim 28.

The adapter includes front slot opening 30 communicating with the third bounding wall 24 of central bore 18 and forming therewith diametrally opposed grooves 32 and 34, and thereby defining diametrally opposed retention flange portions 36 and 38 transverse to the slot opening, for engagement with a syringe, as described below. The adapter 10 further includes an adaptive mounting means 40 for engaging and disengaging the adapter 10 from a front-loading injector.

As used herein, the term "diametrally opposed" means that the relevant structural elements are located at opposite sides of a cylindrical or circular element or member of the appertaining apparatus. The diametrally opposed elements or members are thus symmetrically arranged with respect to an associated diameter of the cylindrical or circular part or structure with which they are associated.

Adaptive mounting means 40 allows the adapter to be engaged and disengaged from a front end of an injector. Rear cylindrical extension 14 includes circumferential groove or slot 42 therein. In a preferred embodiment flanges 44 and 46 are diametrally opposed for engaging a matably shaped cavity on a front face of an injector apparatus, and lockable in position by rotation of the adapter so that the diametrally opposed flange elements 44 and 46 engage retaining flange elements in the face of the injector apparatus. Thus, the adapter is adapted to be mounted on a front-load injector apparatus of the type described in U.S. Pat. No. 5,383,858 issued Jan. 24, 1995 to David M. Reilly, et al. and in U.S. Pat. No. 5,520,653 issued May 28, 1996 to David M. Reilly, et al.

Figure 2:
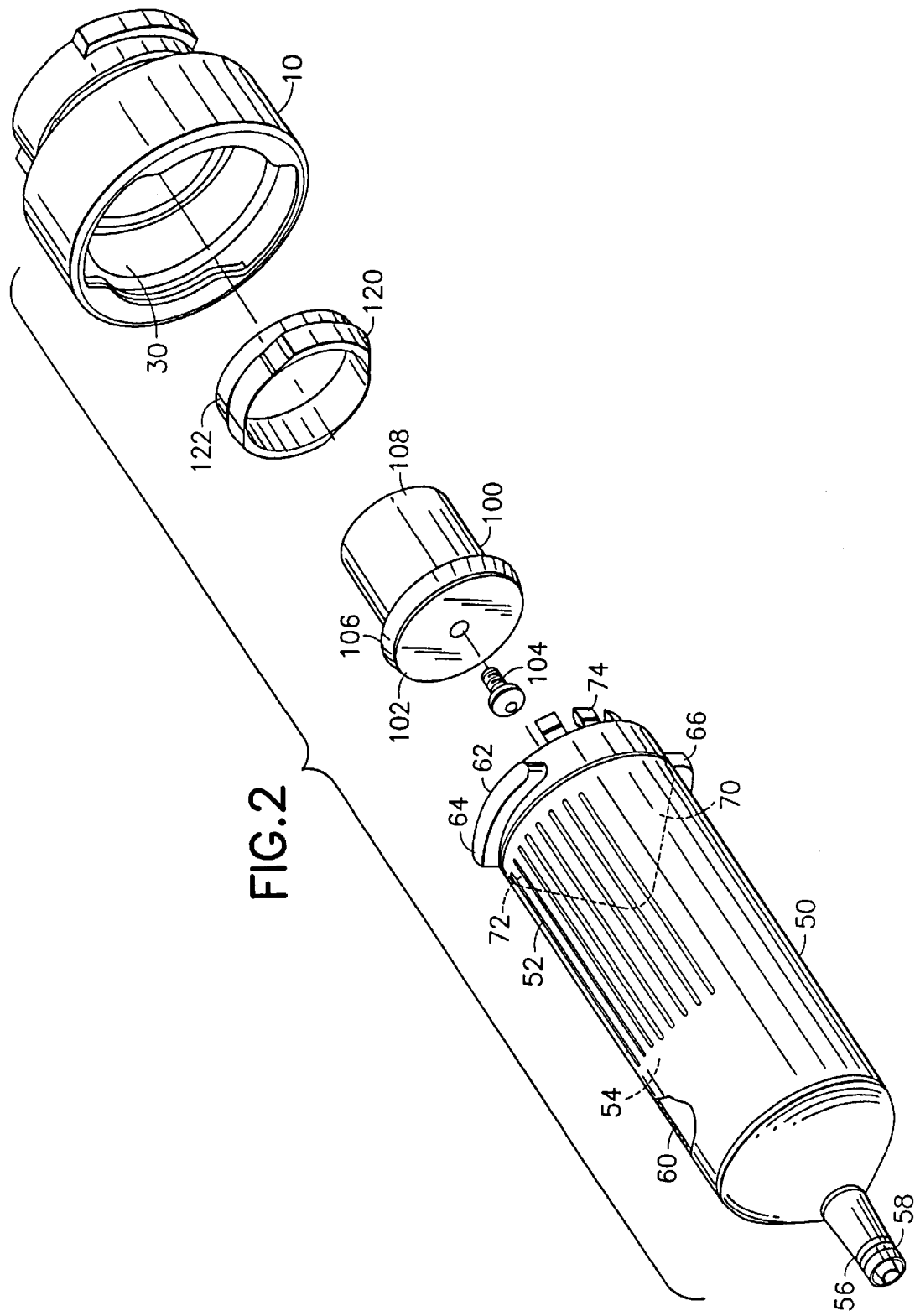
FIG. 2 is a perspective, disassembled view of an injector adapter kit according to another embodiment of the invention.

FIG. 2 is a perspective, disassembled view of an injector adapter kit according to one embodiment of the invention.

The injector retrofit kit described herein is adapted to be detachably engaged to a ram or reciprocating shaft of a front-loaded injector. The injector adapter kit may comprise a syringe 50, a driving head 100, a lifting ring 120, and an adapter 10 as shown in FIG. 1.

As shown in FIG. 2, the syringe 50 includes a main cylindrical barrel 52 enclosing an inner volume 54 which in use of the syringe is filled with contrast media or other solution or liquid to be dispensed through the distal end 56 of the syringe. At its distal end, the syringe is provided with threading 58 in its interior surface, for connection of the distal end of the syringe to a catheter by means of luer-lock or other conventional coupling means.

The interior volume 54 of the syringe is bounded by an interior wall surface 60, as shown. At the proximal end 62 of the syringe is interiorly disposed a plunger 70 according to one embodiment of the present invention. The plunger 70 is of generally converging shape at its distal end, and includes an outer circumferentially continuous edge (side) surface 72 which contacts the inner wall surface 60 of the syringe. The plunger further includes at least two diametrally opposed arrays of spaced-apart flexible resilient engagement members 74, as hereinafter more fully described.

At the proximal end of the syringe on the exterior surface thereof are provided diametrally opposed flange or lug members 64 and 66, for engaging and locking the syringe to the adapter 10, as described below.

Driving head 100 is of frustoconical shape, having a front circular surface 102 with a central set screw 104 therein, and a frustoconical side surface 106. The driving head includes cylindrical collar 108. By means of the central set screw 104, soft tip set screw 107 and soft tip set screw 105 in the cylindrical collar 108, the driving head may be secured to a ram or reciprocating shaft of an injector for forward driving and rearward retraction movement of the ram tip and driving head mounted thereon.

Lifting ring 120 has a cylindrical collar 122 which, in one embodiment, is constructed and arranged in a press fit relationship with the rear first bounding wall 20 of the central bore 18 in rear cylindrical extension 14. The lifting ring 120 radially outwardly deforms the flexible resilient engagement members 74 of the plunger 70 so that the flexible resilient engagement members thereby interact with the adapter to permit engagement (and correspondingly, upon retraction of the ram tip and driving head, disengagement) of the plunger with the driving head.

By the arrangement shown, the front-load angiographic syringe is rearwardly inserted with the flange members 64 and 66 engaging slot 30 in the adapter 10. After positioning in the slot, the syringe is rotated 90°, to lockingly engage flange members 64 and 66 with the internal groove communicating with the slot and forming a retention flange transverse to the direction of slot 30.

Such engagement of the syringe with adapter causes the flexible resilient engagement members 74 to be spread by the lifting ring 120 so that the frustoconical driving head 100 then engages the flexible resilient engagement members to thereby couple the syringe through the plunger to the driving head, for subsequent forward translation of the driving head to express contrast media for other fluid from the syringe barrel interior volume through the distal end of the syringe.

The lifting ring may as shown in FIG. 2 include outwardly extending shoulder elements that are diametrally opposite one another, so that the lifting ring has unshouldered circumferential portions that are diametrally opposite one another and that are between the shoulder elements. The flexible resilient engagement members 74 of the syringe plunger 70 may or may not engage the lifting ring depending on orientation. Upon installation of the syringe, the flexible resilient engagement members 74 of the syringe plunger 70 engage the frustoconical side surface 106 of the driving head and the plunger is thereby subsequently forwardly driveable to advance the plunger in the angiographic syringe and effect delivery of contrast medium to the patient.

The syringe plunger, after such advancement to the distal end of the interior passage in the syringe barrel, may be uncoupled from the catheter or patient line connected to the distal end of the syringe. Thereafter the plunger is retractable in the interior passage of the syringe barrel. Once the plunger is fully retracted, the syringe and plunger may be rotated to contact the flexible resilient engagement members 74 with the shoulders of the lifting ring, thereby spreading the flexible resilient engagement members 74 so that the plunger can be disengaged from the driving head.

Thus, when the flexible resilient engagement members 74 are contacted with the shouldered portions of the lifting ring, they are spread radially outwardly, and when the flexible resilient engagement members 74 overlie the unshouldered portions of the lifing ring, such members are in a retracted state for engagement with the driving head and associated ram tip.

Figure 3:
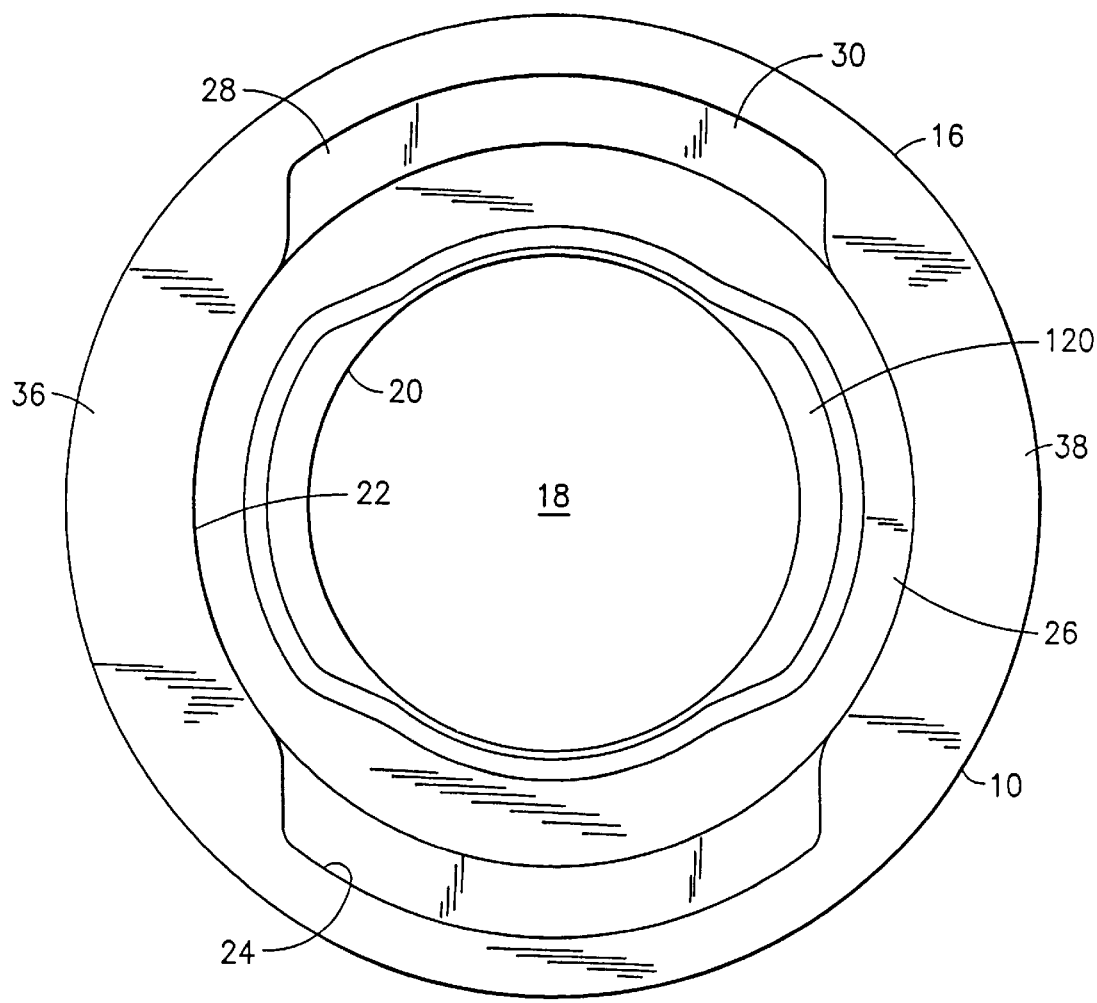
FIG. 3 is a front elevation view of an adapter and lifting ring assembly according to another embodiment of the present invention.

FIG. 3 is a front elevation view of the adapter 10 and lifting ring 120 of FIG. 2 wherein the corresponding structural elements of the adapter are numbered identically. While the lifting ring 120 is shown and described as press fitted into the adapter 10, those skilled in the art will recognize the adapter and lifting ring could be integrally formed as a single component. The lifting ring may be suitably constructed to be of varying form, and may be constructed as shown in FIG. 2 with diametrally opposed lifting shoulder elements, or alternatively with a circumferentially continuous shoulder element.

Figure 4:
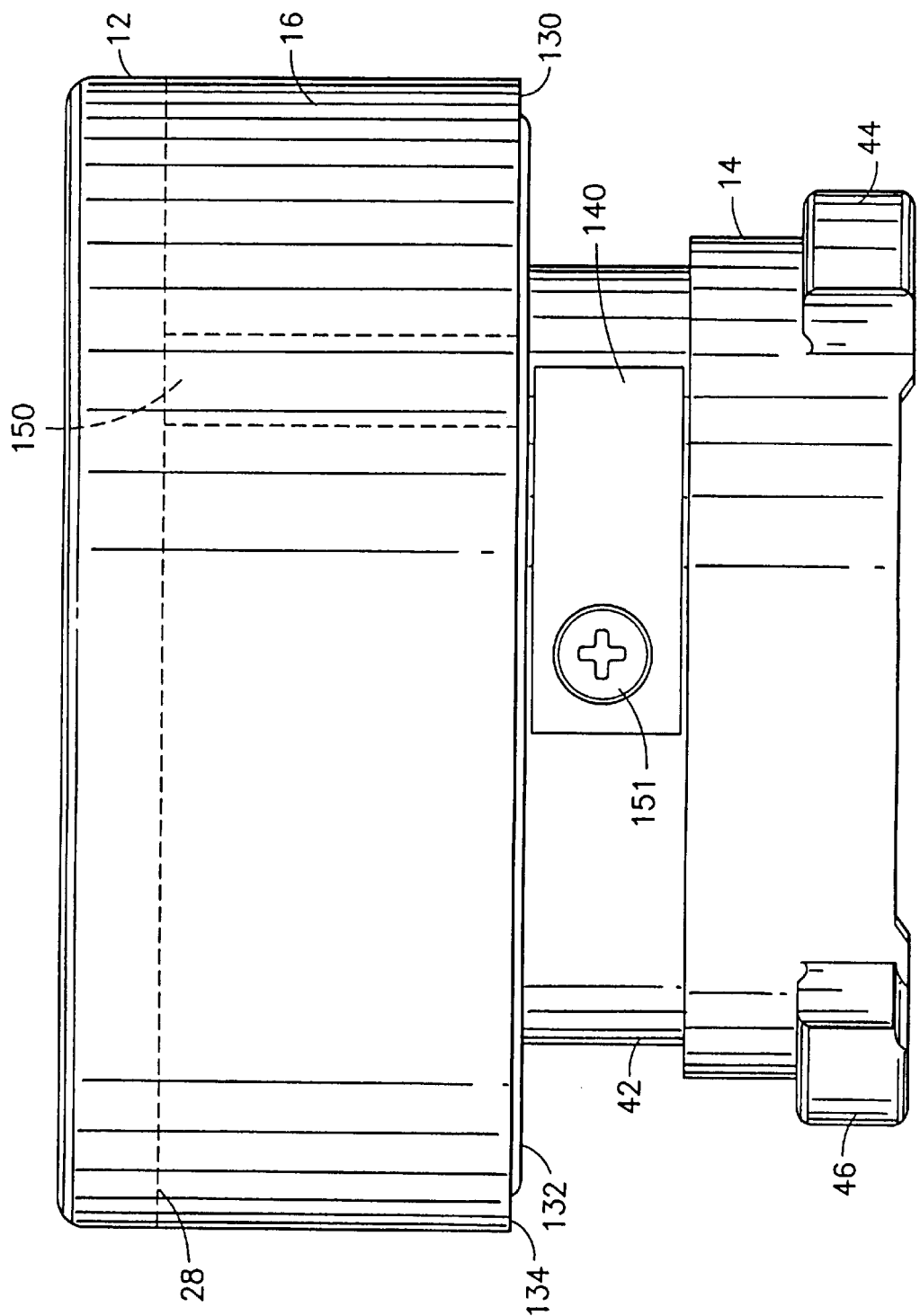
FIG. 4 is a side elevation view of an adapter according to another embodiment of the invention.

FIG. 4 is a side elevation view of an adapter according to another embodiment of the invention, wherein corresponding structural elements of the adapter are numbered identically to FIG. 1. Adapter ring main body 12 has mounted thereon or integrally formed therewith rear cylindrical extension 14. Cylindrical side wall surface 16 and circumferential groove 42 are shown. The main body 12 is of larger diameter than rear cylindrical extension 14, and the junction of the main body and the rear cylindrical extension 14 define a rear face 130. Diametrally opposed flanges 44 and 46 engage a suitably matably shaped cavity on a front face of an injector apparatus, and are lockable by rotation of the main body 12 so that the diametrally opposed flanges 44 and 46 engage retaining flange elements in the face of the injector apparatus. A means for sealing the adapter to the injector is provided, and shown as O-ring 132 disposed in a circumferential groove 134 in the rear face 130. In an alternative embodiment, a gasket or flat washer may be utilized on a flat surface of the rear face to effect sealing in place of the o-ring and groove arrangement.

In this embodiment the adapter includes locking means for positionally maintaining the adapter in a locked position. In the FIG. 4 embodiment, the locking means includes at least one stainless steel leaf spring 140. Leaf spring 140 is secured at an end within circumferential groove 42 and cantilevers tangentially therefrom. During rotational engagement of the adapter to the matably shaped cavity on the front face of the injector apparatus, features within the injector cavity depress each leaf spring. Once the adapter has been rotated into a final, installed position, a recess in the injector cavity allows the leaf spring to flare outward and return to a substantially undepressed condition. With the adapter rotated to the installed position within the cavity, the now-undepressed leaf spring acts as a pawl or detent against the recess to prevent back rotation, opposite to the direction of rotation for installation, and thus prevent removal of the adapter from the injector.

If the adapter must be removed from the injector, a slot 150 would allow access to each leaf spring. Slot 150 extends longitudinally from second annular rim 28 (shown as a dotted hidden line in FIG. 4) to rear face 130 and allows a screwdriver, or other suitable tool, to be inserted into the slot and used to depress the leaf spring while the adapter is in the installed position. Once the leaf spring is depressed, the leaf spring no longer acts a pawl or detent and the adapter may be rotated opposite to the direction of rotation for installation, and affect removal of the adapter from the injector.

The slot 151 could, alternatively, only partially extend longitudinally from rear face 130 to second annular rim 28. This embodiment would maintain a thin solid section between the second annular rim 28 and the slot 150 extending from rear face 130. The slot would, therefore, not be noticeable from a frontal view of the adapter. If access to the leaf springs was desired, this thin solid section would then be removed by "knocking out" the section. A screwdriver, or other suitable tool, would then be inserted into the slot and used to depress the leaf spring for subsequent removal.

Although the leaf spring 140 is shown secured by screw 150, other means for securing the leaf spring within circumferential groove 42 include welding, brazing, bonding, and other similar mechanical/chemical securing methods.

Those skilled in the art will recognize leaf spring 140 can have a variety of cambers, such as a flat camber or a concave/convex camber, and the particular camber design of the leaf spring can be chosen without undue experimentation.

The adapter, lifting ring, and leaf spring may be constructed of stainless steel, aluminum, plastic or any other alternative materials of construction, as will be appreciated by those skilled in the art. For example, the adapter and lifting ring could be molded from a plastic material. Additionally, locking means other than the leaf spring could be used, such as detent structures, matable interlocks, spring-biased expansion structures, pivot arms, heat expandable structures or chemicals, etc. With structures such as pivot arms, the adapter may be correspondingly fabricated with machined pockets or cavities containing the pivot arms.

Figure 5:
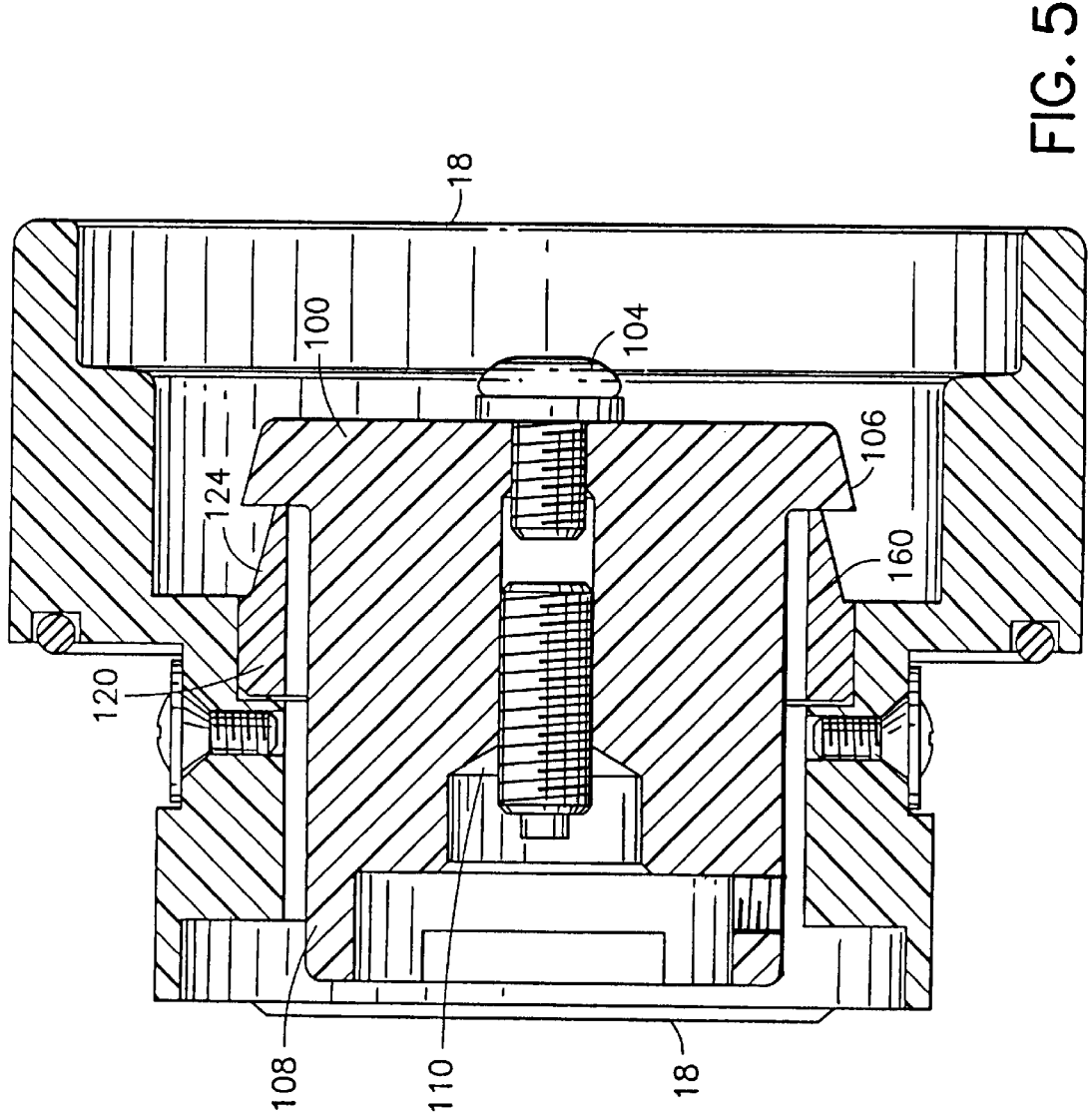
FIG. 5 is a cross-sectional view of an adapter of the type shown in FIG. 4.

FIG. 5 is a cross-sectional view of the adapter of FIG. 4, showing the lifting ring 120 press fit into the adapter and showing the driving head 100 disposed within central bore 18. The lifting ring 120 is press fit into adapter central bore 18 and forms the annular volume 160 which receives the proximal extremity of the syringe of FIG. 2, with the lifting ring having a beveled outer surface 124 as shown, which serves to engage with the flexible resilient engagement members (as shown in FIG. 2) of the plunger and to radially outwardly deform such engagement members for subsequent engagement with the frustoconical driving head which is forwardly advanced into engagement with the plunger.

The driving head includes a frustoconical side surface 106 (as previously described in connection with FIG. 2) and collar 108. The frustoconical driving head has a central bore 110 therein for receiving set screw 104 and soft tip set screw 105, as shown. A side bore is provided in the collar 108 for the soft tip set screw 105.

Figure 6:
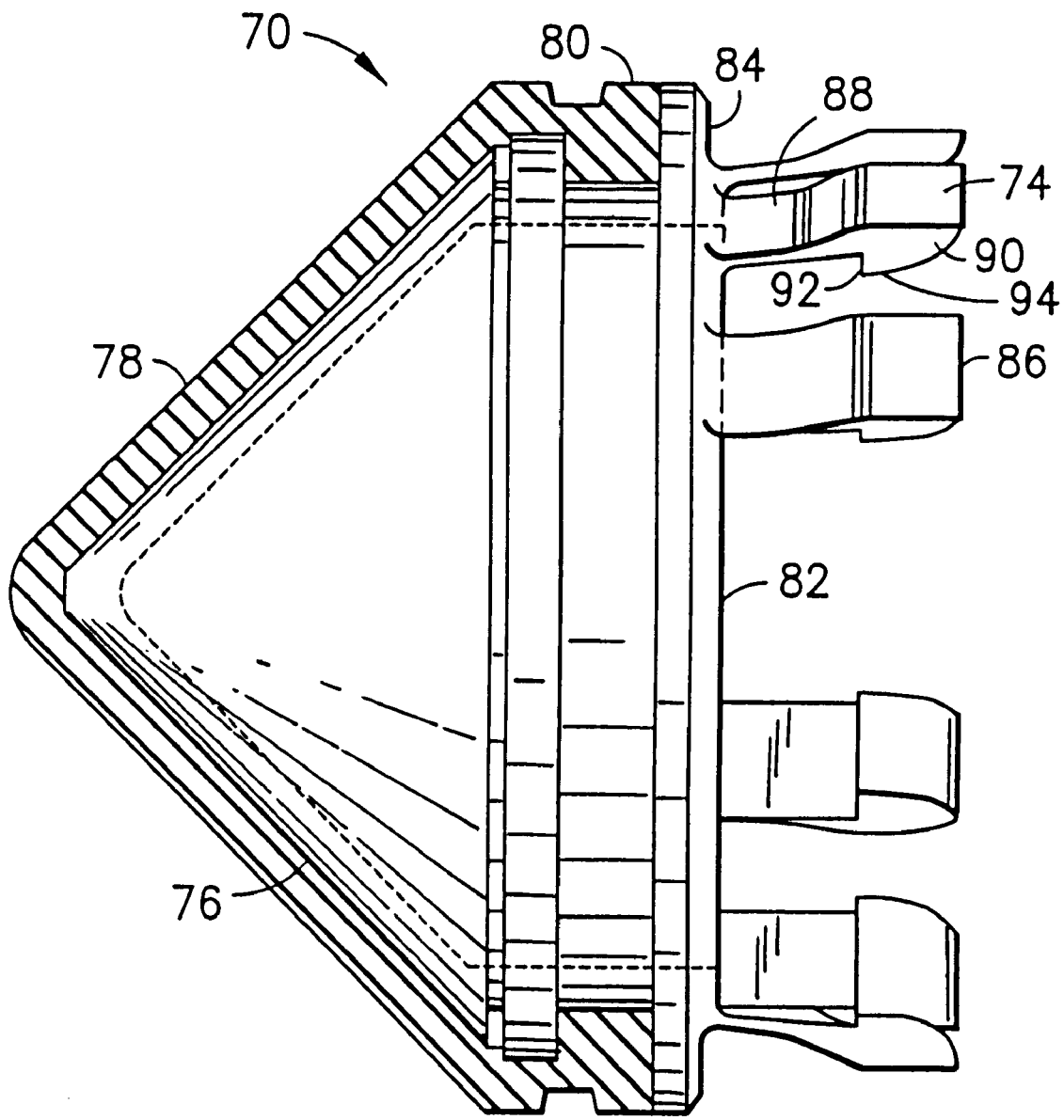
FIG. 6 is a side elevation view of a plunger according to one embodiment of the present invention.

FIG. 6 is a side elevation view of a plunger 70 according to one embodiment of the present invention. The plunger in this embodiment includes a plunger body 76 which may be overlaid by a resilient rubber or hard plastic cover 78 which may be stretch-fitted over the plunger body 76 as shown. Alternatively, the plunger body may be a unitary one piece design without any cover or sheath member. The plunger body with the cover has an outer circumferentially continuous edge surface 80 for engaging an interior surface of the syringe barrel when the plunger is operatively positioned within the syringe barrel.

The proximal face 82 of the plunger body includes a circumferential surface portion 84. An array of diametrally opposed spaced-apart flexible resilient engagement members 74 is joined to the circumferential surface portion 84 of the proximal face of the plunger body and rearwardly extends therefrom to a rearmost extremity 86. Each of the flexible resilient members has a shank portion 88 rearwardly extending from the circumferential surface portion 84 and terminating in a tail hook portion 90 including a transversely and radially inwardly extending retention surface 92 for matably engaging with a rear circumferential surface of the driving head of the injector when the driving head is operatively coupled with the plunger. Each tail hook portion at the retention surface 92 is of increased thickness (in the lateral dimension transverse to the length dimension of the flexible resilient engagement member) relative to the shank portion 88 of such member. The tail hook portion is of tapering character from the region of the retention surface 92 in the rearward direction toward the rearmost extremity 86 thereof, and the tail hook portion has in the embodiment shown a convexly shaped inner engagement surface 94 for contacting the frustoconical shaped driving head to circumferentially compressively engage the frustoconical side surface of the driving head with the transversely and radially inwardly extending retention surface 92 engaged with a rear circumferential surface of the driving head when the driving head is engaged with the plunger. The array of flexible resilient engagement members 74 is diametrally opposed on the circumferential surface portion 84 of the proximal face 82 of the plunger body so that the flexible resilient engagement members are radially inwardly spaced from the outer circumferentially continuous edge surface of the plunger. The purpose of such radial inset of the engagement members 74 is so that such engagement members do not contact interior surfaces of the syringe barrel during translation of the plunger forwardly or rearwardly through the syringe barrel.

Figure 7:
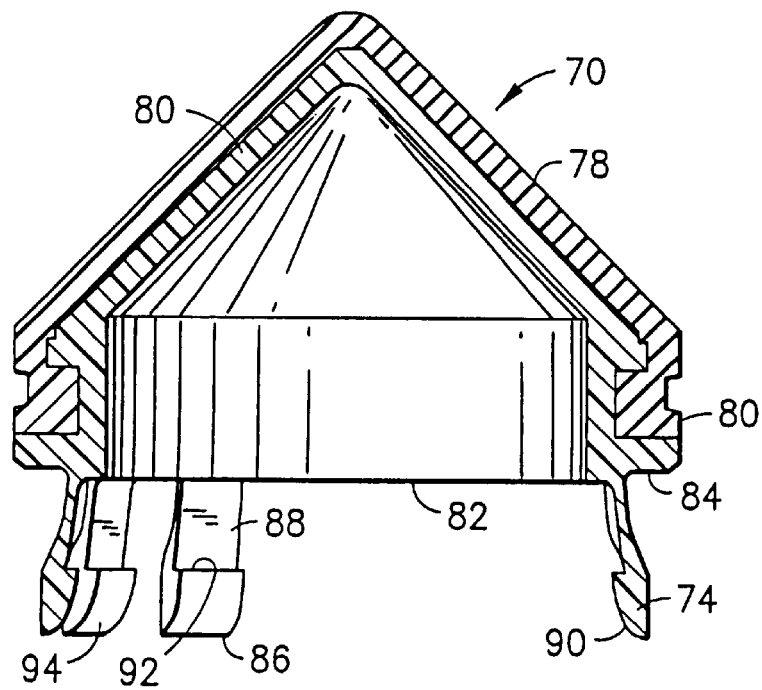
FIG. 7 is a cross-sectional elevation view of a plunger of the type shown in FIG. 6.

FIG. 7 is a cross-sectional elevation view of a plunger of the type shown in FIG. 6 showing the hollowed out interior volume of the plunger body. The plunger alternatively may be of solid-body construction, without such interior cavity.

The plunger body may be formed of any suitable material of construction, such as polyurethane, polyvinylchloride, polymeric rubber or block copolymer composition, or of any suitable material of construction.

Figure 8:
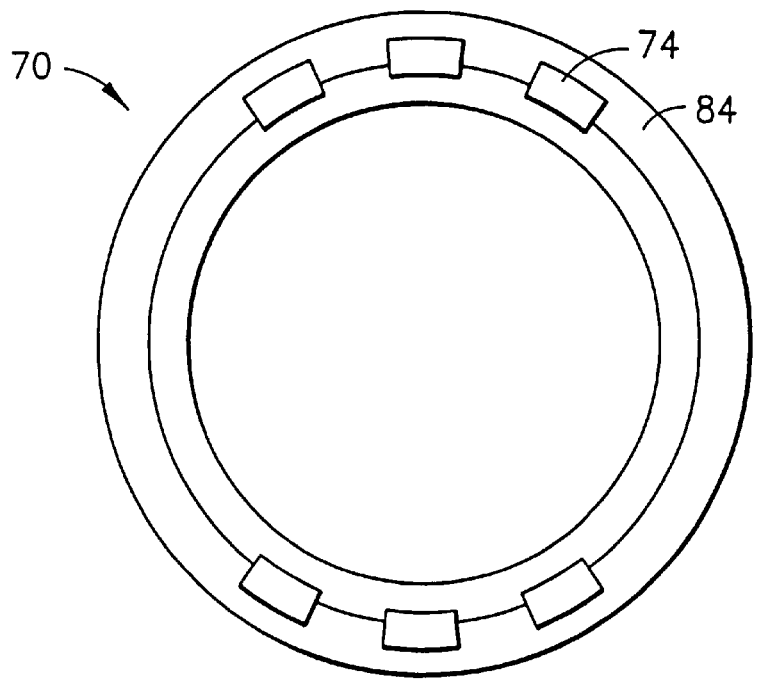
FIG. 8 is a rear view of a plunger of the type shown in FIGS. 6 and 7.

FIG. 8 is a rear plan view of the plunger 70 of FIGS. 6 and 7.

FIG. 9 shows a retrofit kit exploded relationship to an injector apparatus. The corresponding structural elements of the adapter, syringe, lifting ring, and driving head are numbered identically to FIG. 2. The retrofit kit includes at least one component selected from the group consisting of adapter 10, driving head 100, lifting ring 120, and syringe 50 with plunger 70. The injector apparatus 200 as shown comprises an injector housing 202 with a front face 204 to which is secured a face plate adapter assembly 206. The face plate adapter assembly has a front face 208 with a cylindrical cavity 210 therein and a front slot opening 212 communicating therewith. The driving head 100 may be secured to a generally rectangular ram tip mounted on a reciprocating shaft for forward driving and rearward retraction movement of the ram tip 214 and driving head 100 mounted thereon.

By the arrangement shown, the adapter is rearwardly inserted with the flange members 44 and 46 engaging the slot 212 on the face plate adapter assembly 206. After positioning in the slot, the adapter is rotated 90°, to lockingly engage flange members 44 and 46 with an internal groove communicating with the slot and forming a retention flange transverse to the direction of slot 212.

The angiographic syringe 50 is rearwardly inserted with the flange members 64 and 66 engaging the slot 30 on the front face of adapter 10. After positioning in the slot, the syringe is rotated 90°, to lockingly engage flange members 64 and 66 with internal grooves 32 and 34 communicating with the slot and forming a retention flange transverse to the direction of slot 30.

Such engagement of the syringe with the adapter causes the flexible resilient engagement members 74 to be spread by the lifting ring 120 so that the frustoconical driving head then engages the flexible resilient engagement members to thereby couple the syringe through the plunger to the driving head, for subsequent forward translation of the driving head to express contrast media for other fluid from the syringe barrel interior volume through the distal end of the syringe.

The embodiment of the invention variously shown and described with reference to FIGS. 1–9 hereof overcomes the "cocking" problem of various prior art plunger and driving head connection/coupling arrangements, and the various embodiments shown also allow a retrofit kit to be offered for use with various injector designs.

Thus, it will be seen that the present invention contemplates an adapter and retrofit kit for a front-load angiographic syringe injector system, in which the adapter interacts with the injector to effect engagement and disengagement of the adapter, plunger, syringe, and driving head relative to one another.

The present invention also contemplates an angiographic syringe including a plunger of the above-described type.

The present invention further contemplates a front-load injector system comprising an adapter and angiographic syringe including a plunger of the above-described construction.

Thus, while the invention has been described herein with respect to various illustrated features, aspects and embodiments, it will be recognized that the invention is not thus limited, and other variations, modifications and alternative embodiments will readily suggest themselves to those of ordinary skill in the art. Accordingly, the invention is to be broadly construed, consistent with the claims hereafter set forth.

What is claimed is:

1. A front load syringe injector system comprising:
   a. a drive mechanism;
   b. a front-load injector apparatus having mounted on a front face thereof a detachably engageable adapter;
   c. an angiographic syringe mounted on the detachably engageable adapter;
   d. a plunger mounted in the angiographic syringe, wherein the plunger comprises:
      (i) a circumferential surface for engaging the inner surface of a syringe barrel; and
      (ii) a proximal face having attached thereto two or more flexible shank members extending rearwardly therefrom, said flexible shank members comprising a tail hook portion at a rearward terminus of the shank portion, said tailhook portion comprising a retention surface, and said flexible shank members being configured so that they do not touch the syringe barrel upon entry thereinto.

2. The front load syringe injector system of claim 1 wherein the plunger further comprises a conical front face.

3. The front load syringe injector system of claim 1 wherein the flexible shank members are radially positioned around a circumference of the proximal face of the plunger.

4. The front load syringe injector system of claim 1 wherein the plunger comprises 3 or more flexible shank members radially positioned around a circumference of the proximal face of the plunger.

5. The front load syringe injector system of claim 1 wherein the plunger comprises 4 or more flexible shank members radially positioned around a circumference of the proximal face of the plunger.

6. The front load syringe injector system of claim 1, wherein the hook portions of the tail hook members face inwardly.

7. The front load syringe injector system of claim 1 wherein the tail hook portions further comprise an engagement surface curving rearward generally transverse to and away from a terminus of the retention surface, to provide in a general tapering of the tail hook portion from the retention surface to the rearmost extremity.

8. The front load syringe injector system of claim 7 wherein the engagement surface of the engagement members is convexly shaped.

9. The front load syringe injector system of claim 7 configured such that upon contacting a frustoconically shaped driving head, the retention surface compressively engages a frustoconical side surface of the driving head and the retention surface matably engages with a rear circumferential surface of the driving head.

10. The front load syringe injector system of claim 4 wherein the plunger is engageable while the plunger and the engagement members are positioned within the syringe barrel.

11. A front-load syringe injector system, comprising an angiographic syringe including a plunger; the plunger comprising:
   a plunger body having a generally convergent distal portion, an outer circumferentially continuous edge surface for engaging an interior surface of a syringe barrel when the plunger is operatively positioned within the syringe barrel, and a proximal face including a circumferential surface portion, with an array of diametrally disposed spaced-apart flexible, resilient engagement members joined to the circumferential surface portion of the proximal face of the plunger body and extending rearwardly therefrom;
   each of said flexible resilient engagement members having a shank portion rearwardly extending from the circumferential surface portion of the proximal face of the plunger and terminating in a tail hook portion including a transversely and radially inwardly extending retention surface for matably engaging with a rear circumferential surface of a frustoconically shaped drive head of an injector when the drive head is operatively coupled with the plunger, each tail hook portion at the retention surface being of increased thickness relative to the shank portion of the flexible resilient engagement member, and of tapering character toward a rearmost extremity thereof, with a convexly shaped inner engagement surface for contacting the frustoconically shaped driving head to compressively engage a frustoconical side surface of the driving head with the transversely and radially inwardly extending retention surface matably engaged with a rear circumferential surface of the driving head when the driving head is engaged with the plunger; and the spaced-apart flexible resilient engagement members being diametrally opposed on the circumferential surface portion of the proximal face of the plunger so that the flexible resilient engagement members are radially inwardly spaced from the outer circumferentially continuous edge surface of the plunger, whereby the flexible resilient engagement members do not contact interior surfaces of the syringe barrel during translation of the plunger forwardly or rearwardly through the syringe barrel.

12. A front-load syringe injector system comprising:
(a) a drive mechanism;
(b) a front-load injector apparatus having mounted on a front face thereof a detachably engageable adapter;
(c) an angiographic syringe mounted on the detachably engageable adapter;
(d) a plunger mounted in the angiographic syringe, said plunger comprising a plunger body having a generally convergent distal portion, an outer circumferentially continuous edge surface for engaging an interior surface of a syringe barrel when the plunger is operatively positioned within the syringe barrel and a proximal face including a circumferential surface portion with an array of diametrically disposed spaced-apart flexible, resilient engagement members joined to the circumferential surface portion of the proximal face of the plunger body and extending rearwardly therefrom;

each of said flexible resilient engagement members having a shank portion rearwardly extending from the circumferential surface portion of the proximal face of the plunger and terminating in a tail hook portion including a transversely and radially inwardly extending retention surface for matably engaging with a rear circumferential surface of a frustoconically shaped drive head of an injector when the drive head is operatively coupled with the plunger, each tail hook portion at the retention surface being of increased thickness relative to the shank portion of the flexible resilient engagement member, and of tapering character toward a rearmost extremity thereof, with a convexly shaped inner engagement surface for contacting the frustoconically shaped driving head to compressively engage a frustoconical side surface of the driving head with the transversely and radially inwardly extending retention surface matably engaged with a rear circumferential surface of the driving head when the driving head is engaged with the plunger; and the spaced-apart flexible resilient engagement members being diametrally opposed on the circumferential surface portion of the proximal face of the plunger so that the flexible resilient engagement members are radially inwardly spaced from the outer circumferentially continuous edge surface of the plunger whereby the flexible resilient engagement members do not contact interior surfaces of the syringe barrel during translation of the plunger forwardly or rearwardly through the syringe barrel (e) a driving head engaged with the drive mechanism of the injector, such driving head disengageably engaging the plunger.

13. A front load syringe injector system comprising:
a. a drive mechanism;
b. a front-load injector apparatus having mounted on a front face thereof a detachably engageable adapter;
c. an angiographic syringe mounted on the detachably engageable adapter;
d. a plunger comprising:
 (i) a plunger body comprising
  a) a distal portion;
  b) b) an outer circumferentially continuous edge surface for engaging an interior surface of a syringe barrel;
  c) a proximal face generally opposite the distal portion comprising a circumferential surface portion;
 (ii) an array of circumferentially spaced-apart flexible, resilient engagement members joined to the circumferential surface portion of the proximal face of the plunger body and extending rearwardly therefrom, each of said engagement members comprising:
  a) a flexible shank portion rearwardly extending from the circumferential surface portion of the proximal face of the plunger;
  b) a tail hook portion at a rearward terminus of the shank portion comprising:
   (1) a transversely and radially inwardly extending retention surface, having an attachment point and an inner terminus, for matably engaging with a rear circumferential surface of a drive head of an injector when the drive head is operatively coupled with the plunger;
   (2) a convexly shaped inner engagement curving rearward generally transverse to and outwardly from the terminus of the retention Surface, resulting in a general tapering of the tail hook portion from the retention surface to the rearmost extremity, such that upon contacting a frustoconically shaped driving head, the retention surface can compressively engage a frustoconical side surface of the driving head and the retention surface matably engaged with a rear circumferential surface of the driving head; and
 wherein the spaced apart flexible resilient engagement members:
  (i) are diametrically opposed on the circumferential surface portion of the proximal face of the plunger so that the flexible resilient engagement members are radially inwardly spaced from the outer circumferentially continuous edge surface of the plunger;
  (ii) are inwardly biased; and
  (iii) do not contact interior surfaces of a syringe barrel during translation of the plunger forwardly or rearwardly through the syringe barrel.

14. A front-load syringe injector system comprising:
a. a drive mechanism;
b. a front-load injector apparatus having mounted on a front face thereof a detachably engageable adapter comprising
 (i) means for attaching the adapter to the front-load injector apparatus;
 (ii) a cavity extending through the adapter, arranged such that during operation the driving mechanism moves the driving head through the cavity; and (iii) means for attaching a syringe to the adapter; and
c. an angiographic syringe mounted on the detachably engageable adapter;
d. a plunger mounted in the angiographic syringe, said plunger comprising:
  (i) a circumferential surface for engaging the inner surface of a syringe barrel; and
  (ii) a proximal face having attached thereto two or more shank members extending rearwardly therefrom, said flexible shank members comprising a tail hook portion at a rearward terminus of the shank portion, said tailhook portion comprising a retention surface, and said flexible shank members being configured such that such members do not touch the syringe barrel upon entry thereinto.

15. The front-load syringe injector system of claim 14 wherein the plunger further comprises a conical front face.

16. The front-load syringe injector system of claim 14 wherein the flexible shank members are radially positioned around the circumference of the proximal face of the plunger.

17. The front-load syringe injector system of claim 14 wherein the plunger further comprises 3 or more flexible shank members radially positioned around the circumference of the proximal face of the plunger.

18. The front-load syringe injector system of claim 14 wherein the plunger further comprises 4 or more flexible shank members radially positioned around the circumference of the proximal face of the plunger.

19. The front-load syringe injector system of claim 14 wherein the hook portions of the plunger face inwardly.

20. The front-load syringe injector system of claim 14 wherein the tail hook portions of the plunger further comprise an engagement surface curving rearward generally transverse to and outwardly from a terminus of the retention surface, to provide a general tapering of the tail hook portion from the retention surface to the rearmost extremity.

21. The front-load syringe injector system of claim 20 wherein the engagement surface is convexly shaped.

22. The front-load syringe injector system of claim 14 wherein the plunger is configured such that upon contacting a frustoconically shaped driving head, the retention surface compressively engages a frustoconical side surface of the driving head and the retention surface matably engages with a rear circumferential surface of the driving head.

23. The front-load syringe injector system of claim 14 wherein the plunger is configured such that the plunger is engageable while the plunger is positioned within the syringe barrel such that the hook members no not extend outside the syringe barrel.

24. The front-load syringe injector system of claim 14 wherein the face plate further comprises a lifting ring positioned such that as the plunger is fully retracted, the lifting ring engages the convexly shaped inner engagement surface and forces the tailhook portions to disengage the driving head.

25. The front-load syringe injector system of claim 24 wherein the lifting ring comprises a conical side face for engagement with the convexly shaped inner engagement surface of the tail hook portions.

26. The front-load syringe injector system of claim 14 wherein the adapter comprises:
  a. means for forcing the tail hook portions outward upon initial engagement with the inner engagement surface; and
  b. means to permit the tail hook portions to flex inwardly as the driving head is moved from the position of initial engagement to a position of locking engagement with the driving head.

27. The front-load syringe injector system of claim 20 wherein the adapter comprises:
  a. means for forcing the tail hook portions outward upon initial engagement with the inner engagement surface; and
  b. means to permit the tail hook portions to flex inwardly as the driving head is moved from the position of initial engagement to a position of licking engagement with the driving head; and
  c. a lifting ring positioned such that as the plunger is fully retracted, the lifting ring engages the engagement surface, thereby forcing the tailhook portions to disengage the driving head.

28. An adapter for interconnecting an angiographic syringe with an injector, said adapter comprising:
  a main body having a rear cylindrical extension, with a central bore extending through the main body and the rear cylindrical extension;
  the rear cylindrical extension including diametrally opposed flanges for engaging a matably shaped cavity on a front face of an injector apparatus, and lockable in position by rotation of the main body so that the diametrally opposed flange elements engage retaining flange elements in the face of the injector apparatus;
  the main body having a front slot opening communicating with the central bore, the front slot opening having diametrally opposed retention flange portions transverse to the slot opening, for engagement with a front-load syringe having rear flange members engageable with the slot opening and lockable in position in the main body by rotation so that the rear flange members of the syringe engage the retention flange portions of the main body;
  the main body having a lifting ring defining an annular volume between the central bore and the lifting ring for engagement with a rear circumferential extremity of a syringe;
  and the rear cylindrical extension including a locking means, so that when the main body is rotated to a final, installed position the locking means interacts with features in the injector cavity and prevents backrotational removal of the adapter.

29. An adapter for interconnecting an angiographic syringe with an injector according to claim 28, wherein the locking means is selected from the group consisting of leaf springs, detents, pivot arms, expansion elements, and heat expandable elements.

30. An adapter for interconnecting an angiographic syringe with an injector, said adapter comprising:
  a main body having a rear cylindrical extension, with a central bore extending through the main body and the rear cylindrical extension;
  the rear cylindrical extension including diametrally opposed flanges for engaging a matably shaped cavity on a front face of an injector apparatus, and lockable in position by rotation of the main body so that the diametrally opposed flange elements engage retaining flange elements in the face of the injector apparatus;
  the main body having a front slot opening communicating with the central bore, the front slot opening having diametrally opposed retention flange portions transverse to the slot opening, for engagement with a front-load syringe having rear flange members engageable with the slot opening and lockable in position in the main body by rotation so that the rear flange members of the syringe engage the retention flange portions of the main body;

the main body having a lifting ring defining an annular volume between the central bore and the lifting ring for engagement with a rear circumferential extremity of a syringe;

and the rear cylindrical extension including at least one leaf spring secured to a surface of the adapter and cantilevering tangentially therefrom, so that during rotational engagement of the main body with the matably shaped cavity of the injector, features within the cavity depress the leaf spring, and when the main body is rotated to a final, installed position a recess in the injector cavity allows the leaf spring flare outward and prevent backrotational removal of the adapter.

31. The adapter for interconnecting an angiographic syringe with an injector according to claim 30, wherein the main body includes a means for sealing a rear face of the main body to the front face of the injector.

32. The adapter for interconnecting an angiographic syringe with an injector according to claim 31, wherein the means for sealing a rear face of the main body to the front face of the injector comprises a sealing means selected from the group consisting of (I) an o-ring disposed in a circumferential groove in the rear face, (II) a gasket on a flat surface of the rear face, and (III) a flat washer on a flat surface of the rear face.

33. A plunger having utility in a power-driven angiographic syringe assembly comprising power driving means including an axially extending reciprocatable drive shaft and a frustoconically shaped driving head attached to said drive shaft, the plunger comprising:

a plunger body having a generally convergent distal portion, an outer circumferentially continuous edge surface for engaging an interior surface of a syringe barrel when the plunger is operatively positioned within the syringe barrel, and a proximal face including a circumferential surface portion, with an array of diametrally disposed spaced-apart flexible, resilient engagement members joined to the circumferential surface portion of the proximal face of the plunger body and extending rearwardly therefrom;

each of said flexible resilient engagement members having a shank portion rearwardly extending from the circumferential surface portion of the proximal face of the plunger and terminating in a tail hook portion including a transversely and radially inwardly extending retention surface for matably engaging with a rear circumferential surface of a drive head of an injector when the drive head is operatively coupled with the plunger, each tail hook portion at the retention surface being of increased thickness relative to the shank portion of the flexible resilient engagement member, and of tapering character toward a rearmost extremity thereof, with a convexly shaped inner engagement surface for contacting the frustoconically shaped driving head to compressively engage a frustoconical side surface of the driving head with the transversely and radially inwardly extending retention surface matably engaged with a rear circumferential surface of the driving head when the driving head is engaged with the plunger; and wherein the spaced-apart flexible resilient engagement members:

(a) are diametrally opposed on the circumferential surface portion of the proximal face of the plunger so that the flexible resilient engagement members are radially inwardly spaced from the outer circumferentially continuous edge surface of the plunger;

(b) are inwardly biased; and (c) do not contact interior surfaces of the syringe barrel during translation of the plunger forwardly or rearwardly through the syringe barrel.

34. An angiographic syringe comprising a plunger according to claim 33.

35. An angiographic retrofit kit, comprising:

an angiographic syringe including a plunger; the plunger comprising:

a plunger body having a generally convergent distal portion, an outer circumferentially continuous edge surface for engaging an interior surface of a syringe barrel when the plunger is operatively positioned within the syringe barrel, and a proximal face including a circumferential surface portion, with an array of diametrally disposed spaced-apart flexible, resilient engagement members joined to the circumferential surface portion of the proximal face of the plunger body and extending rearwardly therefrom;

each of said flexible resilient engagement members having a shank portion rearwardly extending from the circumferential surface portion of the proximal face of the plunger and terminating in a tail hook portion including a transversely and radially inwardly extending retention surface for matably engaging with a rear circumferential surface of a frustoconically shaped drive head of an injector when the drive head is operatively coupled with the plunger, each tail hook portion at the retention surface being of increased thickness relative to the shank portion of the flexible resilient engagement member, and of tapering character toward a rearmost extremity thereof, with a convexly shaped inner engagement surface for contacting the frustoconically shaped driving head to compressively engage a frustoconical side surface of the driving head with the transversely and radially inwardly extending retention surface matably engaged with a rear circumferential surface of the driving head when the driving head is engaged with the plunger; and the spaced-apart flexible resilient engagement members being diametrally opposed on the circumferential surface portion of the proximal face of the plunger so that the flexible resilient engagement members are radially inwardly spaced from the outer circumferentially continuous edge surface of the plunger, whereby the flexible resilient engagement members do not contact interior surfaces of the syringe barrel during translation of the plunger forwardly or rearwardly through the syringe barrel.

36. An angiographic retrofit kit according to claim 35, further comprising an adapter, the adapter comprising:

a main body having a rear cylindrical extension, with a central bore extending through the main body and the rear cylindrical extension;

the rear cylindrical extension including diametrally opposed flanges for engaging a matably shaped cavity on a front face of an injector apparatus, and lockable in position by rotation of the main body so that the diametrally opposed flange elements engage retaining flange elements in the face of the injector apparatus;

the main body having a front slot opening communicating with the central bore, the front slot opening having diametrally opposed retention flange portions transverse to the slot opening, for engagement with a front-load syringe having rear flange members engageable with the slot opening and lockable in position in the main body by rotation so that the rear flange members of the syringe engage the retention flange portions of the main body;

the main body having a lifting ring defining an annular volume between the central bore and the lifting ring for engagement with a rear circumferential extremity of a syringe;

and the rear cylindrical extension including a locking means, so that when the main body is rotated to a final, installed position the locking means interacts with features in the injector cavity and prevents backrotational removal of the adapter.

37. An angiographic retrofit kit, the kit comprising at least one component selected from the group consisting of an adapter, a syringe and plunger, and a driving head;

the adapter comprising a main body having a rear cylindrical extension, with a central bore extending through the main body and the rear cylindrical extension;

the rear cylindrical extension including diametrally opposed flanges for engaging a matably shaped cavity on a front face of an injector apparatus, and lockable in position by rotation of the main body so that the diametrally opposed flange elements engage retaining flange elements in the face of the injector apparatus;

the main body having a front slot opening communicating with the central bore, the front slot opening having diametrally opposed retention flange portions transverse to the slot opening, for engagement with a front-load syringe having rear flange members engageable with the slot opening and lockable in position in the main body by rotation so that the rear flange members of the syringe engage the retention flange portions of the main body;

the main body having a lifting ring defining an annular volume between the central bore and the lifting ring for engagement with a rear circumferential extremity of a syringe;

and the rear cylindrical extension including a locking means, so that when the main body is rotated to a final, installed position the locking means interacts with features in the injector cavity and prevents backrotational removal of the adapter;

an angiographic syringe including a plunger, the plunger including
a plunger body having a generally convergent distal portion, an outer circumferentially continuous edge surface for engaging an interior surface of a syringe barrel when the plunger is operatively positioned within the syringe barrel, and a proximal face including a circumferential surface portion, with an array of diametrally disposed spaced-apart flexible, resilient engagement members joined to the circumferential surface portion of the proximal face of the plunger body and extending rearwardly therefrom;

each of said flexible resilient engagement members having a shank portion rearwardly extending from the circumferential surface portion of the proximal face of the plunger and terminating in a tail hook portion including a transversely and radially inwardly extending retention surface for matably engaging with a rear circumferential surface of a drive head of an injector when the drive head is operatively coupled with the plunger, each tail hook portion at the retention surface being of increased thickness relative to the shank portion of the flexible resilient engagement member, and of tapering character toward a rearmost extremity thereof, with a convexly shaped inner engagement surface for contacting the frustoconical shaped driving head to compressively engage a frustoconical side surface of the driving head with the transversely and radially inwardly extending retention surface matably engaged with a rear circumferential surface of the driving head when the driving head is engaged with the plunger; and the spaced-apart flexible resilient engagement members being diametrally opposed on the circumferential surface portion of the proximal face of the plunger so that the flexible resilient engagement members are radially inwardly spaced from the outer circumferentially continuous edge surface of the plunger, whereby the flexible resilient engagement members do not contact interior surfaces of the syringe barrel during translation of the plunger forwardly or rearwardly through the syringe barrel;

the driving head comprising a front circular surface and a frustoconical side surface, wherein the driving head is secured to a ram or reciprocating shaft of the injector for forward driving and rearward retraction movement of the ram tip and driving head mounted thereon.

38. A front-load syringe injector system including a front-load injector apparatus having mounted on a front face thereof a detachably engageable adapter according to claim 28.

39. An angiographic retrofit kit comprising:
a. a syringe barrel, and
b. a plunger comprising:
(i) a circumferential surface for engaging the inner surface of a syringe barrel; and
(ii) a proximal face having attached thereto two or more flexible shank members extending rearwardly therefrom, said flexible shank members comprising a tail hook portion at a rearward terminus of the shank portion, said tailhook portion comprising a retention surface, and said flexible shank members being configured such that such members do not touch the syringe barrel upon entry thereinto.

40. The angiographic retrofit kit of claim 39 wherein the plunger further comprises a conical front face.

41. The angiographic retrofit kit of claim 39 wherein the flexible shank members are radially positioned around the circumference of the proximal face of the plunger.

42. The angiographic retrofit kit of claim 39 wherein the plunger further comprises 3 or more flexible shank members radially positioned around the circumference of the proximal face of the plunger.

43. The angiographic retrofit kit of claim 39 wherein the plunger further comprises 4 or more flexible shank members radially positioned around the circumference of the proximal face of the plunger.

44. The angiographic retrofit kit of claim 39 wherein the hook portions of the plunger face inwardly.

45. The angiographic retrofit kit of claim 39 wherein the tail hook portions of the plunger further comprise an engagement surface curving rearward generally transverse to and away from a terminus of the retention surface, to provide a general tapering of the tail hook portion from the retention surface to the rearmost extremity.

46. The angiographic retrofit kit of claim 45 wherein the engagement surface is convexly shaped.

47. The angiographic retrofit kit of claim 39 wherein the plunger is configured such that, upon contacting a frustoconically shaped driving head, the retention surface compressively engages a frustoconical side surface of the driving head and the retention surface matably engages with a rear circumferential surface of the driving head.

48. The angiographic retrofit kit of claim 39 wherein the plunger is configured such that the plunger is engageable while the plunger and the engagement members are positioned within the syringe barrel.

* * * * *

UNITED STATES PATENT AND TRADEMARK OFFICE
CERTIFICATE OF CORRECTION

PATENT NO. : 6080136
DATED : June 27, 2000
INVENTOR(S) : Michael Wayne Trull, et al.

It is certified that error appears in the above-indentified patent and that said Letters Patent is hereby corrected as shown below:

Column 2, line 19 change "plunder" to -- plunger --

Column 4, line 38 and line 39 change "extension ma y include an outer surf ace circumferential" to -- extension may include an outer surface circumferential --

Column 4, line 61 change "the pre sent" to -- the present--

Column 7, line 34 change "set screw 105 in the" to -- set screw 105 (soft tip set screws shown in FIG. 5) in the --

Column 9, line 19 change "slot 151" to -- slot 150 --

Column 9, line 29 and line 30 change "screw 150" to -- screw 151 --

UNITED STATES PATENT AND TRADEMARK OFFICE
CERTIFICATE OF CORRECTION

PATENT NO. : 6,080,136
DATED : June 27, 2000
INVENTOR(S) : Michael Wayne Trull, et al It is certified that error appears in the above-indentified patent and that said Letters Patent is hereby corrected as shown below:

Column 9, line 64 and line 65 change "soft tip set screw 105, as shown" to -- soft tip set screw 105, as shown in FIG. 5. --

Column 11, line 28 change " contrast media for other" to -- contrast media or other --

Column 14, line 13 change "b) b) an outer" to -- b) an outer --

Column 17, line 16 change "the leaf spring flare outward" to -- the leaf spring to flare outward --

Column 20, line 35 delete "28."

Signed and Sealed this

Seventeenth Day of April, 2001

*Attest:*

NICHOLAS P. GODICI

*Attesting Officer*   *Acting Director of the United States Patent and Trademark Office*